(12) United States Patent
Kucklick

(10) Patent No.: US 11,596,440 B2
(45) Date of Patent: Mar. 7, 2023

(54) ARTHROSCOPIC FLEXIBLE PORTAL CANNULA DEVICE AND DELIVERY SYSTEM

(71) Applicant: Cannuflow, Inc., Scotts Valley, CA (US)

(72) Inventor: Theodore R. Kucklick, Scotts Valley, CA (US)

(73) Assignee: Cannuflow, Inc., Scotts Valley, CA (US)

( * ) Notice: Subject to any disclaimer, the term of this patent is extended or adjusted under 35 U.S.C. 154(b) by 325 days.

(21) Appl. No.: 17/081,259

(22) Filed: Oct. 27, 2020

(65) Prior Publication Data

US 2021/0038257 A1 Feb. 11, 2021

Related U.S. Application Data

(63) Continuation of application No. 16/149,832, filed on Oct. 2, 2018, now Pat. No. 10,813,666, which is a continuation of application No. 15/621,925, filed on Jun. 13, 2017, now Pat. No. 10,085,768, which is a continuation of application No. 14/203,445, filed on Mar. 10, 2014, now Pat. No. 9,675,379.

(60) Provisional application No. 61/775,464, filed on Mar. 8, 2013.

(51) Int. Cl.
A61B 1/32 (2006.01)
A61B 17/34 (2006.01)

(52) U.S. Cl.
CPC ...... *A61B 17/3423* (2013.01); *A61B 17/3421* (2013.01); *A61B 17/3496* (2013.01); *A61B 2017/3466* (2013.01)

(58) Field of Classification Search
CPC ............ A61B 17/3421; A61B 17/3423; A61B 17/3439; A61B 2017/3433; A61B 2017/3435; A61B 2017/345; A61B 2017/3454
USPC ............................ 600/204; 606/99, 108, 323
See application file for complete search history.

(56) References Cited

U.S. PATENT DOCUMENTS 8,313,459 B2 * 11/2012 Kiehne ............ A61M 25/0631
604/110
2010/0168674 A1 * 7/2010 Shaw ................... A61M 39/06
604/164.07

* cited by examiner

Primary Examiner — Eduardo C Robert
Assistant Examiner — Christina NegrelliRodriguez
(74) Attorney, Agent, or Firm — Crockett & Crockett, PC; K. David Crockett, Esq.; Niky Economy Syrengelas, Esq.

(57) ABSTRACT

A flexible cannula device and delivery system for use in arthroscopic surgery. The delivery system engages the flexible cannula from the inside near the distal tip and pushes it into the surgical portal, essentially pulling the proximal portion of the cannula from the distal tip while being pushed from the proximal end with the specialized driver. The delivery system provides for single point engagement at the distal tip as well as a multiplicity of engagement points along the length of the system.

21 Claims, 14 Drawing Sheets

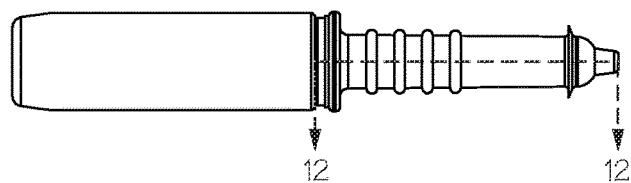
Fig. 11
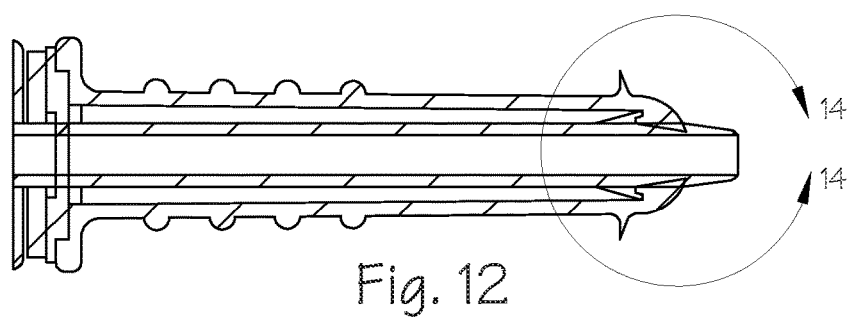
Fig. 12
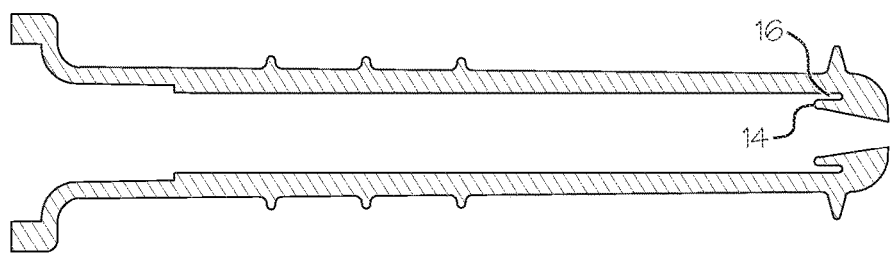
Fig. 13
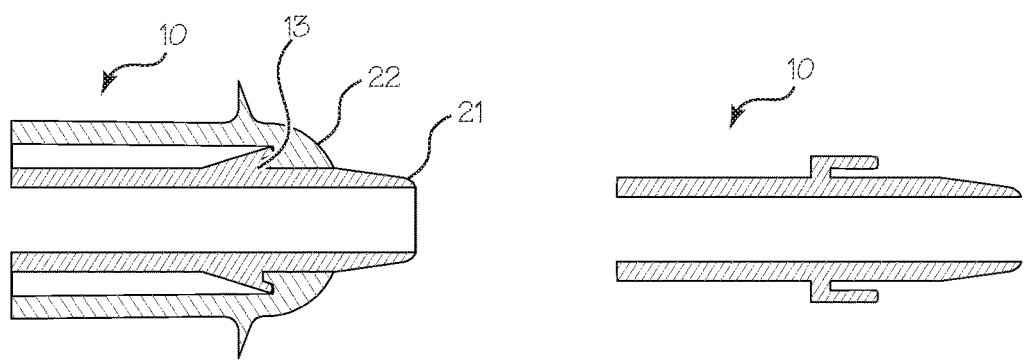
Fig. 14
Fig. 15

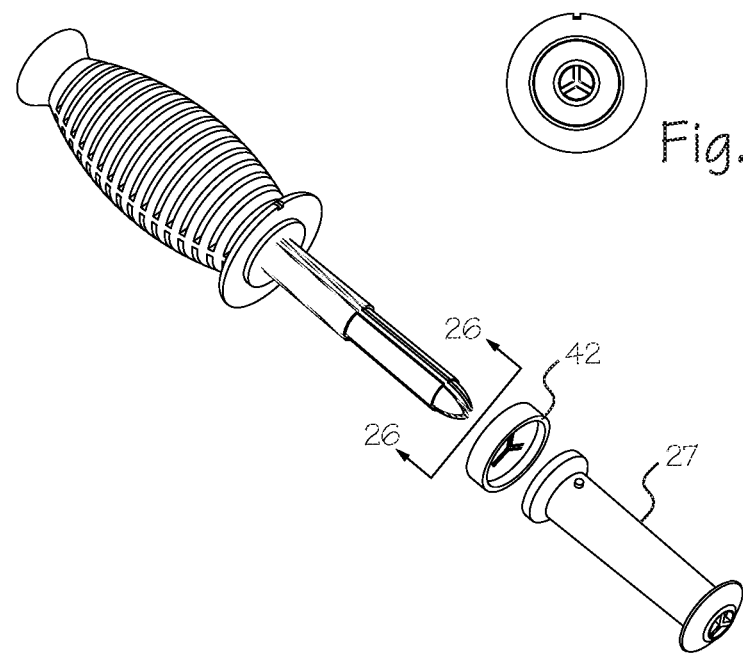

ARTHROSCOPIC FLEXIBLE PORTAL CANNULA DEVICE AND DELIVERY SYSTEM

This application is a continuation of U.S. application Ser. No. 16/149,832, filed Oct. 2, 2018, which is a continuation of Ser. No. 15/621,925, filed Jun. 13, 2017, now U.S. Pat. No. 10,085,768, which is a continuation of U.S. application Ser. No. 14/203,445 filed Mar. 10, 2014, now U.S. Pat. No. 9,675,379, which claims priority to U.S. Provisional Application 61/775,464 filed Mar. 8, 2013.

FIELD OF THE INVENTIONS

The inventions described below relate to the field of arthroscopic surgery and more specifically, to portal access during arthroscopic surgery.

BACKGROUND OF THE INVENTIONS

Arthroscopy is a minimally invasive procedure for treating joint pathology and is a superior alternative to open joint arthrotomy. Arthroscopy has the advantage of less disruption to the joint tissues, and potentially faster healing. The scope of joints and pathologies that can be treated with arthroscopy has grown dramatically, and now includes hip, spine, and small joint procedures in addition to the traditional knee and shoulder procedures. However, arthroscopy remains a technically demanding procedure, and new instrumentation and procedures are constantly being developed. Access to difficult to reach parts of the joint remains a significant challenge. While curved and flexible instruments are available to access these hard to reach areas of the joint, access portal devices have not kept up with the instrument advances. Some attempts have been made to develop flexible portals, however these have significant drawbacks either in being only slightly flexible, being very difficult to use, or being incompatible with standard portal placement techniques and instrumentation. For example, the Arthrex® PassPort Button Cannula™ is a rubbery cannula that provides instrument mobility in shoulder operations. However, delivery of the device is non-standard, requiring the surgeon to fold the device in half with a hemostat before insertion. What is needed is an instrument system that allows a high level of flexibility, high instrument mobility, and high ease of use while retaining compatibility with standard cannula placement techniques involving switching sticks and guide wires.

SUMMARY

The system described below provides for easy insertion of a flexible portal cannula into a surgical portal. The system includes a flexible portal cannula paired with a specialized driver that engages the cannula from the inside near the distal tip and pushes the cannula into the surgical portal, essentially pulling the proximal portion of the cannula from its distal tip while being pushed from the proximal end with the specialized driver. This provides an easy way to put a flexible cannula in place without "pushing a rope" or folding the cannula and forcing it through an incision with a hemostat.

The system may use a single engagement near the distal tip of the portal cannula or a plurality of engagement features distributed along the length of the portal cannula. The engaging features of the portal cannula may, for example, be proximally facing shoulders or an annular flanges, disposed on the inside of the cannula, to create annular grooves, which are paired with distally facing shoulders or projections on the outer surface of a driver. The distally facing shoulders or projections are sized and dimensioned to impact the proximally facing shoulders and/or engage the annular grooves.

The system may use a split driver and corresponding multiple lumen cannula. This system provides for Single Portal Arthroscopy (SPA), which can be used for stitching and passing sutures through one surgical portal, single portal laparoscopic procedures, and passing multiple instruments via a single portal incision.

The system provides a high level of flexibility, high instrument mobility, and high ease of use while retaining compatibility with standard portal placement techniques involving switching sticks and guide wires. The cannula also provides fluid management capability to maintain clarity in the joint. The devices described can be used for all types of arthroscopy including knee, shoulder, hip, small joint, and spine procedures.

BRIEF DESCRIPTION OF THE DRAWINGS

FIG. 11 illustrates the system with an obturator/dilator.

FIG. 12 is a detailed view of the mating engagement between the driver distal end and the cannula of FIG. 9.

FIG. 13 illustrates the cannula.

FIG. 14 illustrates the mating engagement between the obturator distal end and the cannula of FIGS. 11 through 13.

FIG. 15 illustrates an alternate mating engagement feature on an obturator/dilator.

FIG. 25 illustrates an exploded view of a multiple lumen system using multiple engagement features.

FIG. 26 illustrates a detailed view of the multiple lumen system of FIG. 25.

DETAILED DESCRIPTION OF THE INVENTIONS

Figure 1:
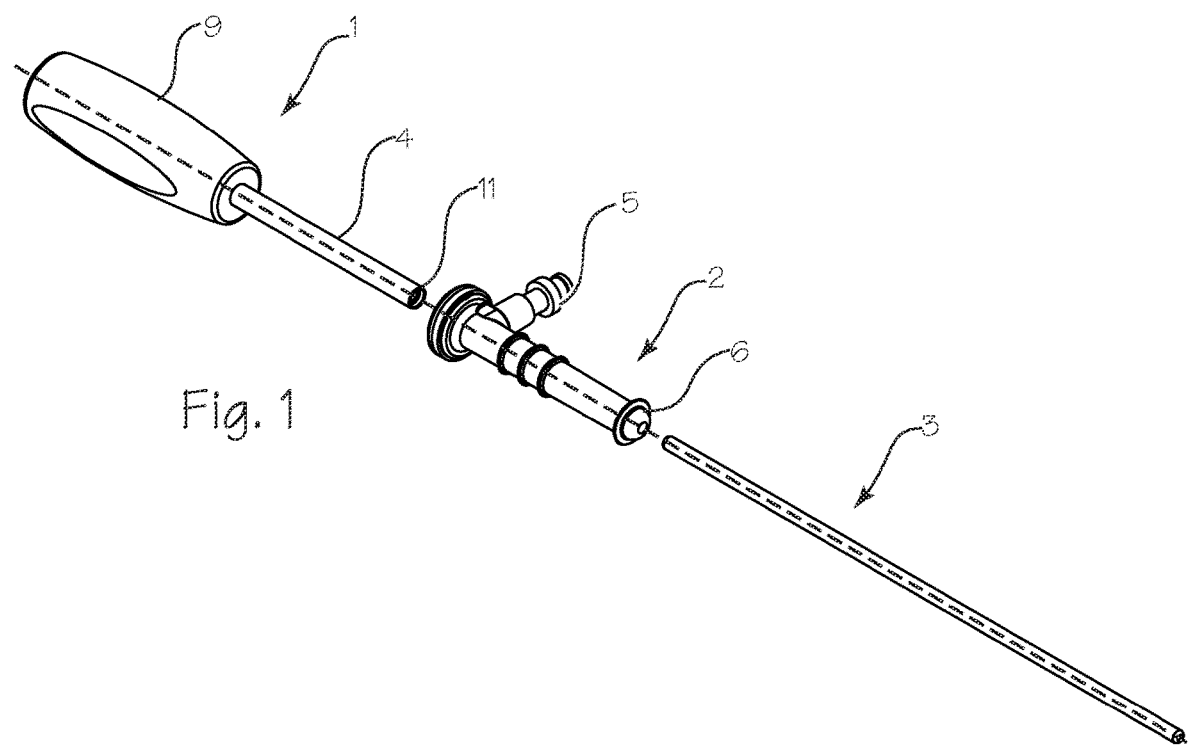
FIG. 1 illustrates an elastomeric portal cannula and driver system with paired engagement features.

FIG. 1 illustrates an exploded view of the system for driving a cannula into a surgical site. The system includes a rigid driver 1, a cannula 2, and a switching stick 3. The cannula is delivered into place with a rigid tube 4 that has an interlocking feature at the distal tip that engages with a mating locking feature in the distal tip of the cannula (further detailed in FIG. 7). In this way, the proximal portion of the cannula is "pulled" into a surgical portal or incision from its distal tip as the distal tip is pushed. The system allows for the use of a "switching stick" or "Wissenger Rod" 3, a rod typically about 4 mm in diameter that is used as a guide wire to place a cannula into a surgical portal. It should be appreciated that the driver cannulation and switching stick is an optional feature.

Figure 2:
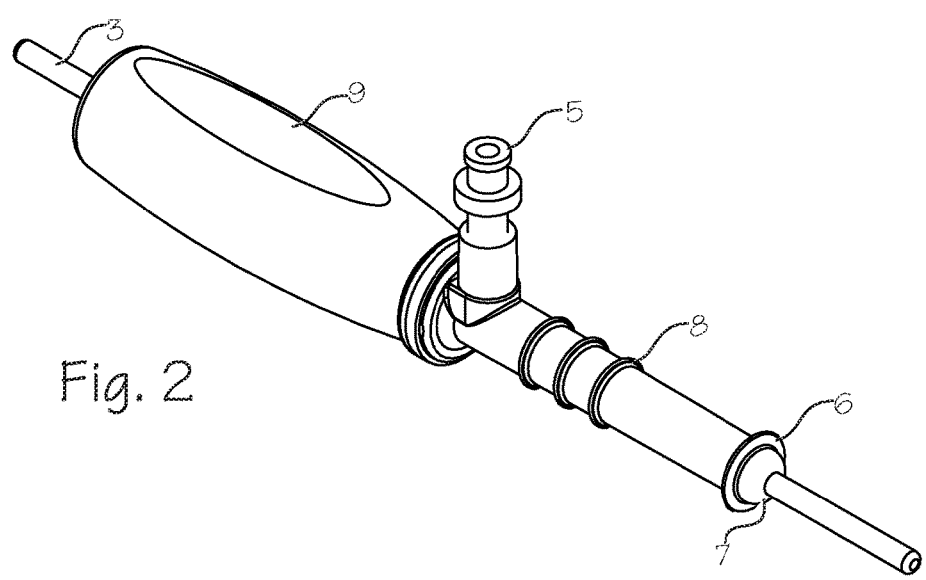
FIG. 2 illustrates the system of FIG. 1 with the driver disposed within the elastomeric portal cannula.

FIG. 2 illustrates the system of FIG. 1 when assembled, with the cannula disposed over the rigid tube. The cannula shown has a side port 5 to allow fluid inflow and outflow from the joint, providing fluid management in order to maintain clarity in the joint during the arthroscopic surgical procedure. The cannula has a flexible distal flange 6 to retain the cannula in the joint, preventing it from backing out of the surgical site. An expandable distal wiper seal 7 may be provided to hold fluid in the joint and prevent fluid leakage. External retention ridges 8 are disposed over the exterior of the cannula.

Figure 3:
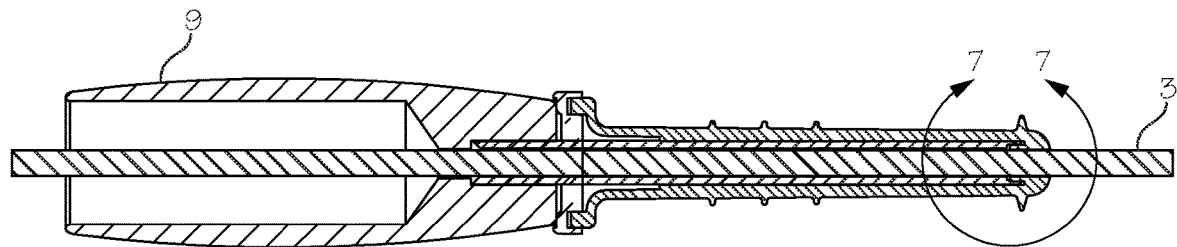
FIG. 3 illustrates the system of FIGS. 1 and 2 with a switching stick disposed within a lumen of a cannulated driver.
Figure 4:
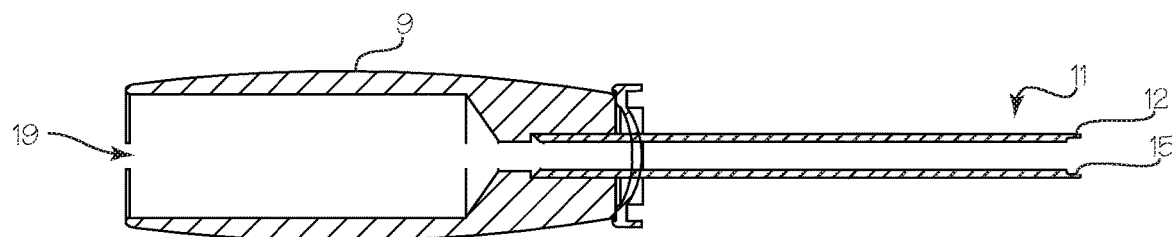
FIG. 4 illustrates the cannulated driver.
Figure 5:
FIG. 5 illustrates the switching stick.

The driver, as shown in FIGS. 3 and 4, comprises a handle 9 attached to the rigid tube 4. The driver maybe cannulated (as shown) through its core to allow for insertion of the switching stick (FIG. 5).

Figure 6:
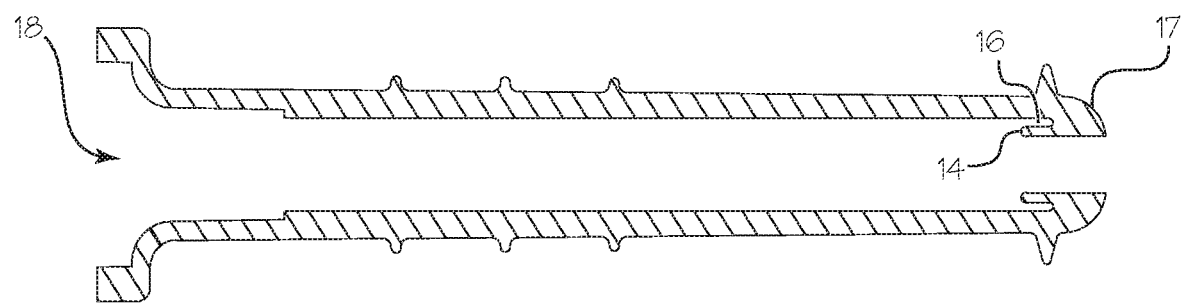
FIG. 6 illustrates the elastomeric portal cannula.
Figure 7:
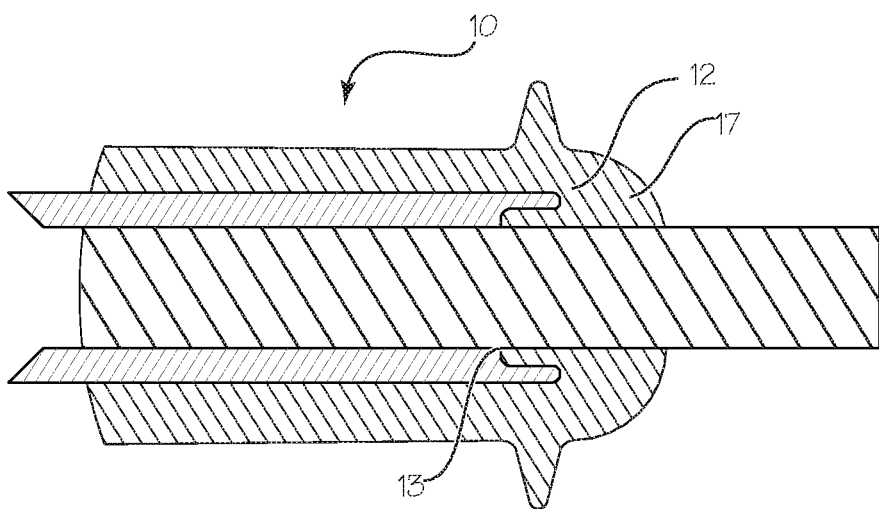
FIG. 7 is a detailed view of the mating engagement between the distal end of the driver and the elastomeric portal cannula.

FIGS. 6 and 7 detail the drive engagement 10 between the cannula and the driver. As shown in FIGS. 4 and 7, the distal tip 11 of the rigid tube of the driver has a distally extending protrusion 12, or segment of tubing, with a larger internal diameter than the remainder of the rigid tube. This creates a distally facing shoulder 13 for engagement with the proximally extending ring 14 of the cannula and distally extending ring 15 on the rigid tube that fits within the annular groove 16 of the cannula. With these components sized and dimensioned to engage each other, the rigid tube can be pushed distally into the cannula until the components are interlocked with the ring 15 disposed with the annular groove 16. Thereafter, the rigid tube and cannula are locked together such that the rigid tube cannot be pushed distally out of the cannula. As shown in FIG. 6, the cannula has a proximally extending lip 17 or ring 14 defining a groove 16 sized and dimensioned to receive the rigid tube distally extending protrusion 12.

In use, the driver is inserted into the proximal end of the cannula 18 until the distally extending protrusion 15 at the distal tip of the rigid driver engages the mating locking feature 16 in the cannula. When the driver is engaged, the cannula is supported by the rigid tube. The switching stick guide rod 3 is driven through the proximal end of the driver 19, through the driver, and out the distal end of the driver. The entire assembly comprising the switching stick, rigid driver and cannula are inserted into the surgical portal or incision. When the cannula is in the desired position in the surgical site, the switching stick is withdrawn, and then the rigid driver is withdrawn.

Figure 8:
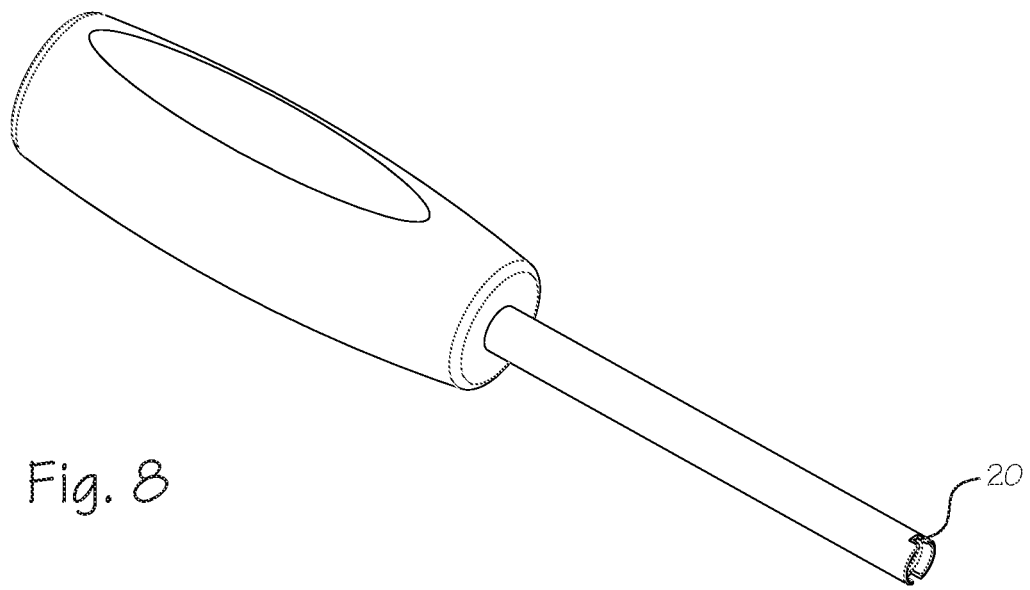
FIG. 8 illustrates a driver with a recess tip.
Figure 9:
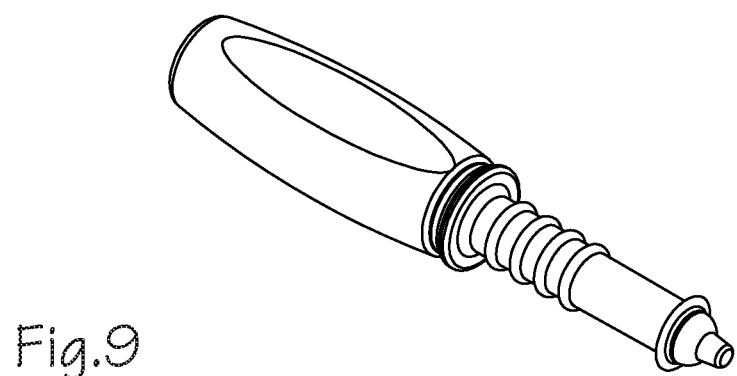
FIG. 9 illustrates a driver with distally extending projections adapted to engage with the features of the inner wall of the elastomeric portal cannula.

Other distal drive mechanisms can be utilized. FIG. 8 illustrates a driver with a recess 20 or slot at its distal tip. The driver with recessed tip engages a protrusion in the interior distal end of the cannula (not shown). Rotation of the driver engages the protrusion in the distal tip of the cannula.

Figure 10:
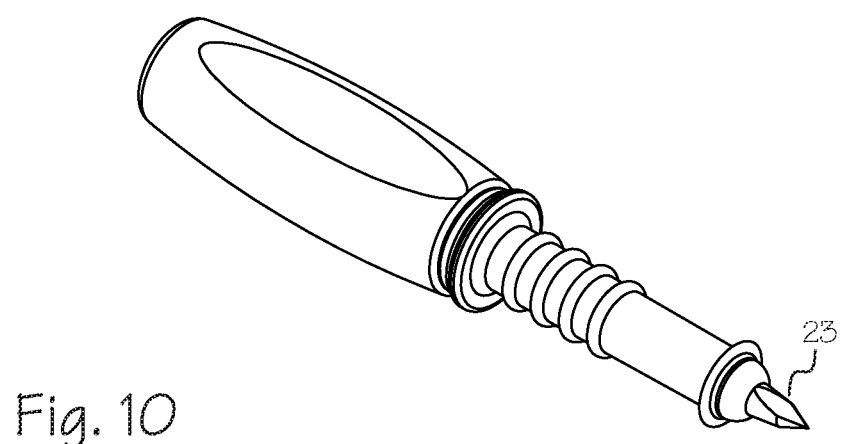
FIG. 10 illustrates the system with a driver with a sharp trocar point.
Figure 16:
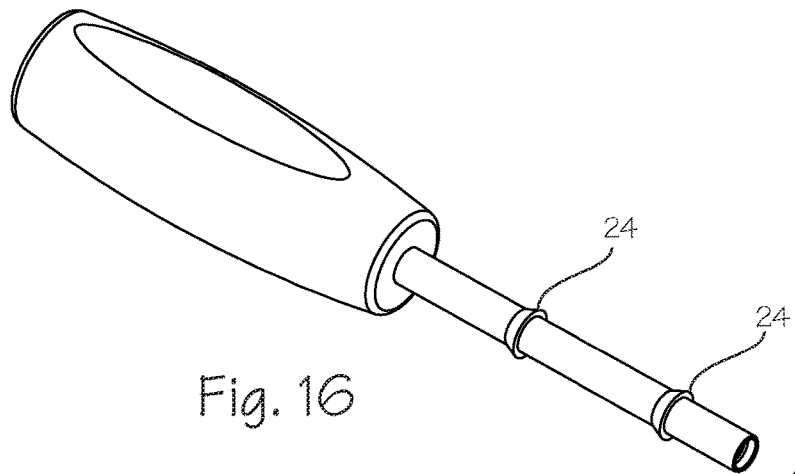
FIG. 16 illustrates an exploded view of a portal cannula and driver system having a plurality of gripping features.
Figure 17:
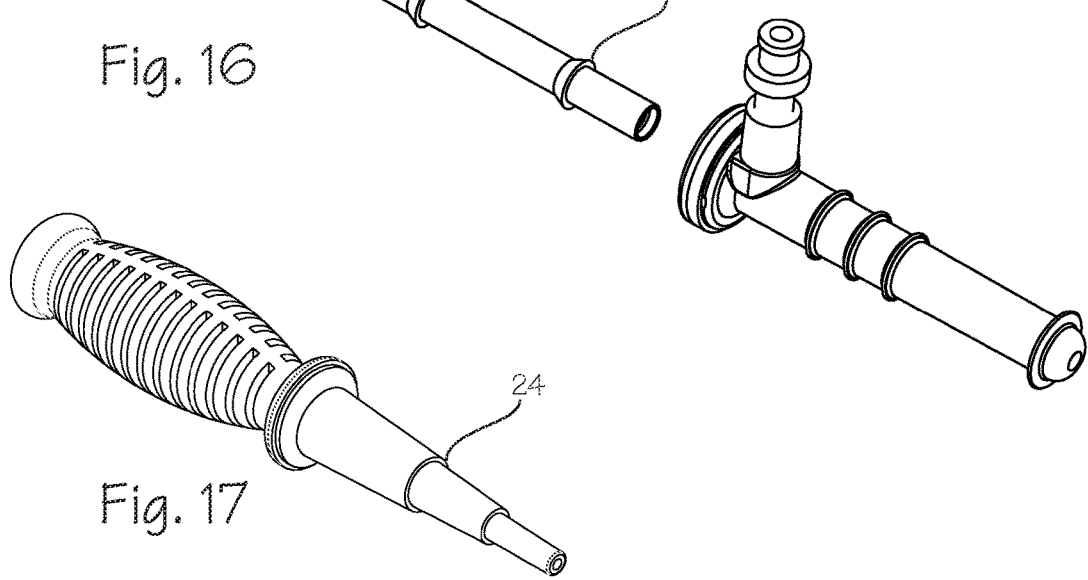
FIG. 17 illustrates a driver with a plurality of cone shaped gripping features.

FIGS. 9 through 14 show embodiments where the driver protrudes out from the distal end of the cannula. Here, the engaging feature 10 on the driver is on the exterior of the rigid tube, rather than the distal extending protrusion as shown in FIGS. 1 through 7). A distally facing shoulder 13 engages with the proximally extending ring 14 of the cannula and distally extending ring 15 on the rigid tube that fits within the annular groove 16 of the cannula. The engagement can be in a flared arrangement as shown in FIG. 14 or more of a rectangular or perpendicular arrangement as shown in FIG. 15. The drive engagement 10 is disposed just proximal to the distal tip of the driver 21 to allow for the distal tip of the driver to extend from the distal tip of the cannula 22. The obturator may be a solid dilator (shown in FIG. 9), allowing the device to penetrate and dilate tough joint capsules like hip joints. The dilator feature protruding from the distal end may be a sharp trocar point 23, as shown in FIG. 10. The protruding portion of the obturator may also be threaded to help in penetrating tough joint capsules, such as the hip capsule. The driver can be a cannulated obturator, with the cannulation being sized to accept a switching stick, a guide wire such as a K-Wire for use in spine surgery, or a nitinol guide wire for use in hip arthroscopy.

Figure 18:
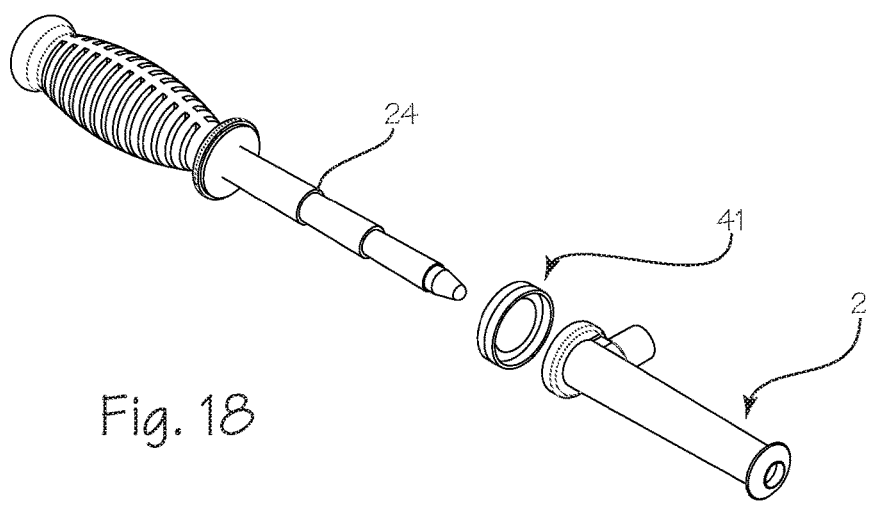
FIG. 18 illustrates an exploded view of the system using a driver with a plurality of cylindrical gripping features.
Figure 19:
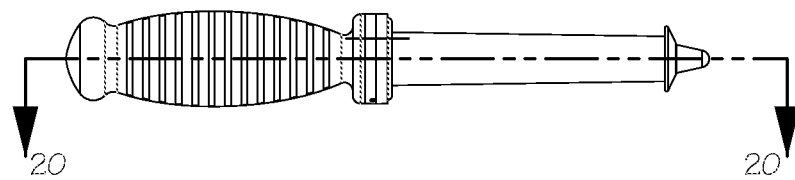
FIG. 19 illustrates the system using a plurality of cylindrical gripping features.
Figure 20:
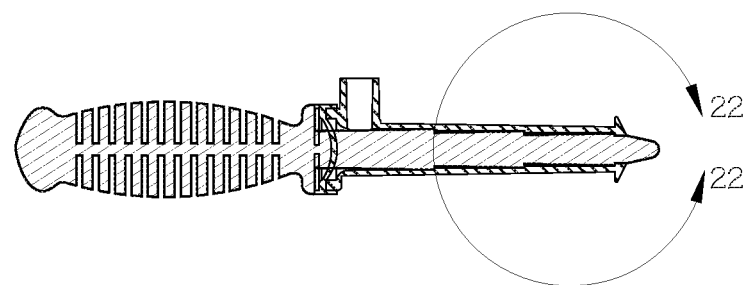
FIG. 20 illustrates the system of FIG. 19 utilizing a plurality of cylindrical gripping features.
Figure 21:
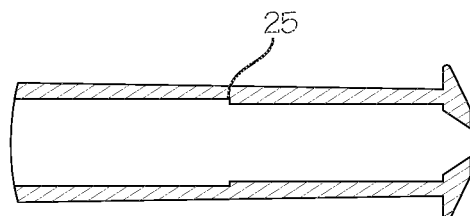
FIG. 21 illustrates the cannula of FIG. 20.
Figure 22:
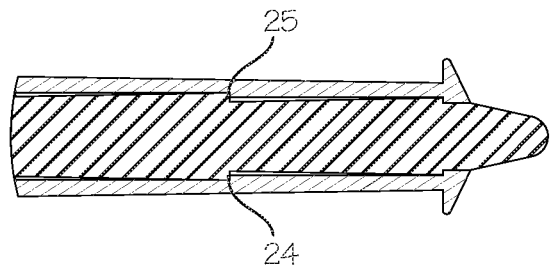
FIG. 22 illustrates the mating engagement between the plurality of cylindrical gripping features and the cannula of FIG. 20.

The driver and cannula can have a plurality of engaging features, as shown in FIGS. 16 through 22. Each of the driver gripping features 24 correspondingly mate with detents 25 disposed on the inside wall of the cannula. Rather than one engagement point at the distal tip, the engagement features are distributed along the length of the cannula. The plurality of engagement features allow the driver to push longer and lower durometer flexible cannulas into a surgical portal. The driver may have a uniform diameter (FIG. 16), graduated stepped cones (FIG. 17), graduated stepped cylinders (FIG. 18), or other multiplicity of engaging features. The distal end of the driver may be flat (FIG. 16 or 17) or cone-shaped (FIG. 18). FIGS. 20 through 22 detail the drive engagement. Distally facing shoulder 24 of the driver engages with a proximally facing shoulder 25 of the cannula.

Figure 23:
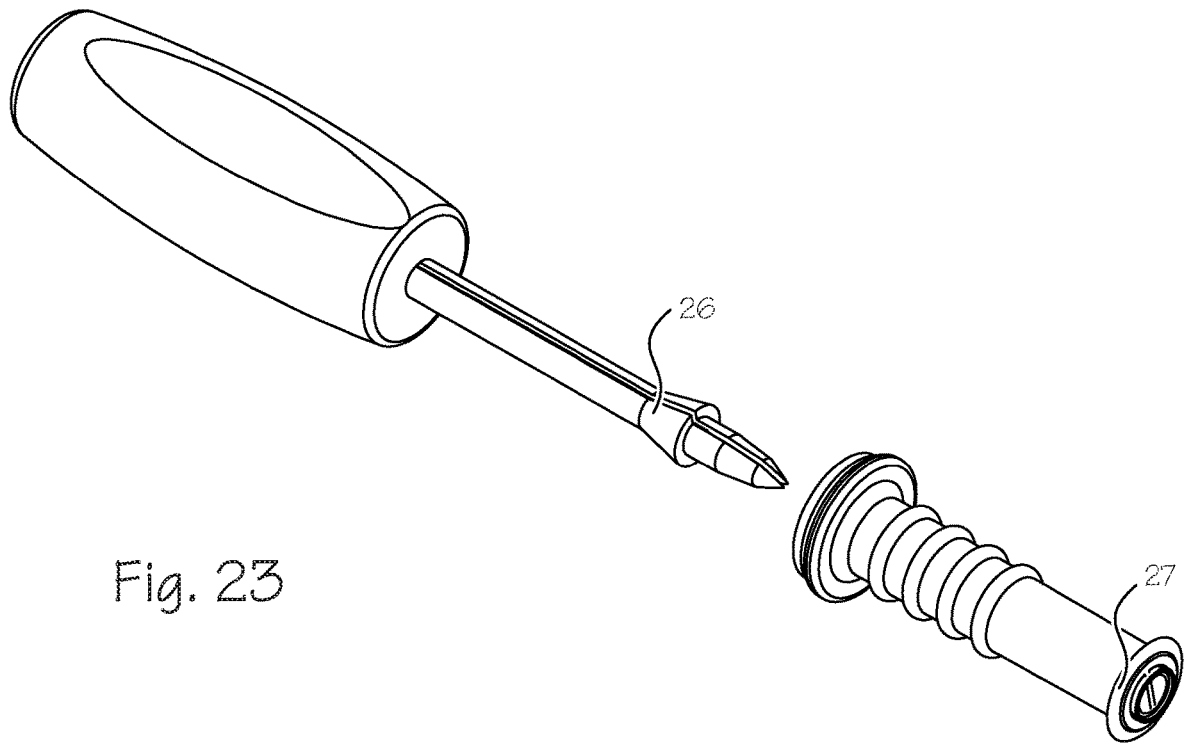
FIG. 23 illustrates an exploded view of a multiple lumen system.
Figure 24:
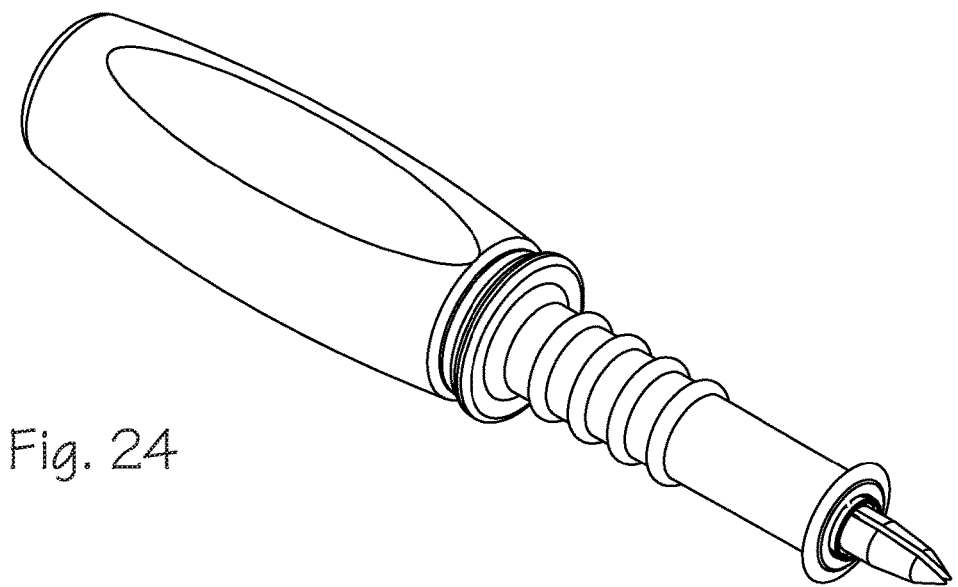
FIG. 24 illustrates the multiple lumen system of FIG. 23.
Figure 27:
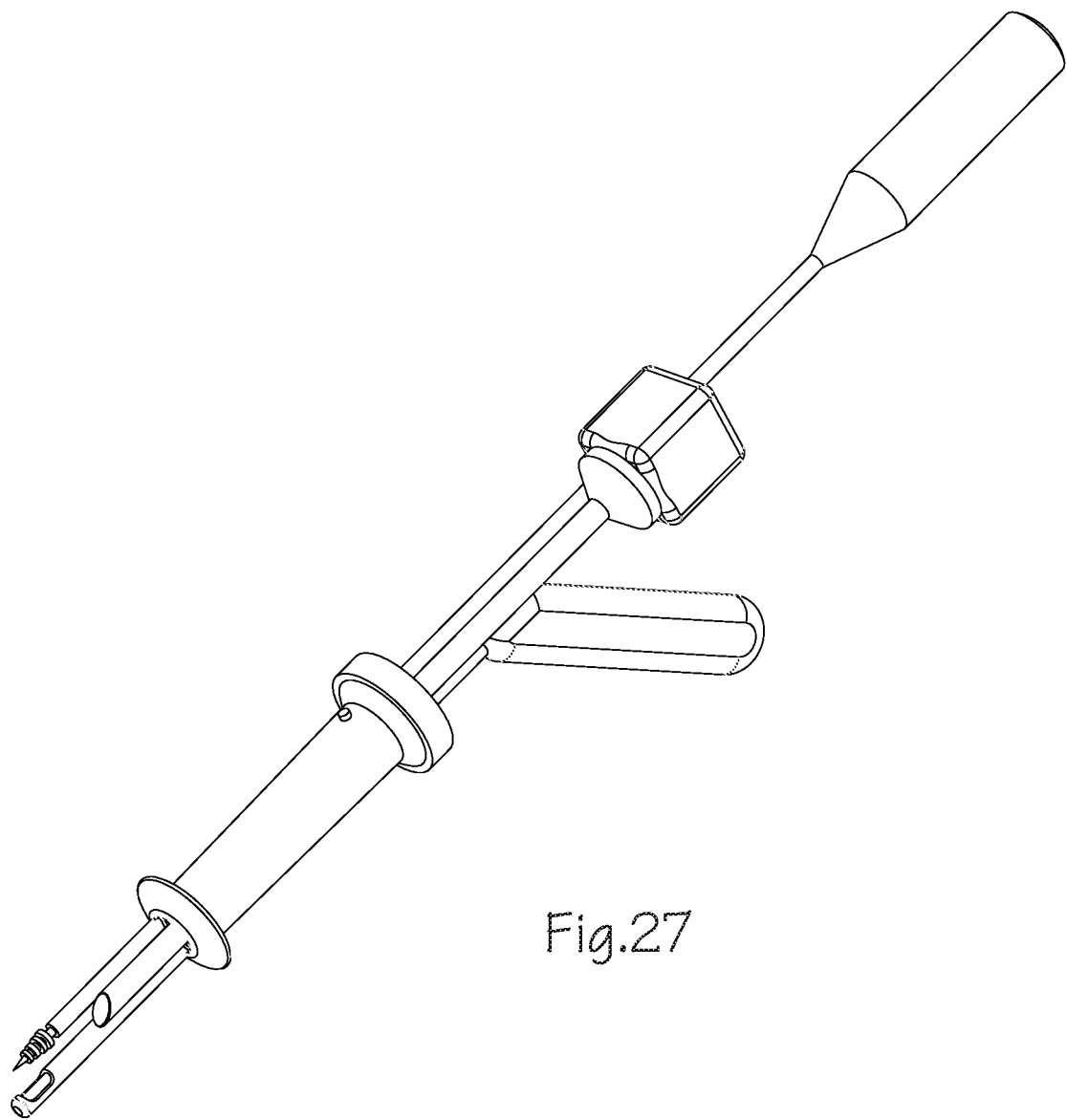
FIG. 27 illustrates the multiple lumen system in use.

FIG. 23 illustrates an exploded view of a multiple lumen system, including a split driver 26 and a multiple lumen cannula 27. The split driver is configured to engage and correspondingly drive a multi-lumen portal. The system can be used for stitching and passing sutures through one portal in an arthroscopic workspace, single portal laparoscopic procedures ("SPL"), and passing multiple instruments via a single portal incision (see FIG. 27). As shown in FIG. 24, the driver is inserted through the cannula. The cannula may have two lumens (FIG. 23), three lumens (FIGS. 25 and 26) or more. The driver will be split in a corresponding way (two for two, three for three, etc.). FIG. 23 illustrates one engagement feature at the distal tip while FIG. 25 shows multiple engagement features 28 along the length of the driver. The alignment mark 29 assists the user in aligning the driver with the lumens of the portal.

Figure 28:
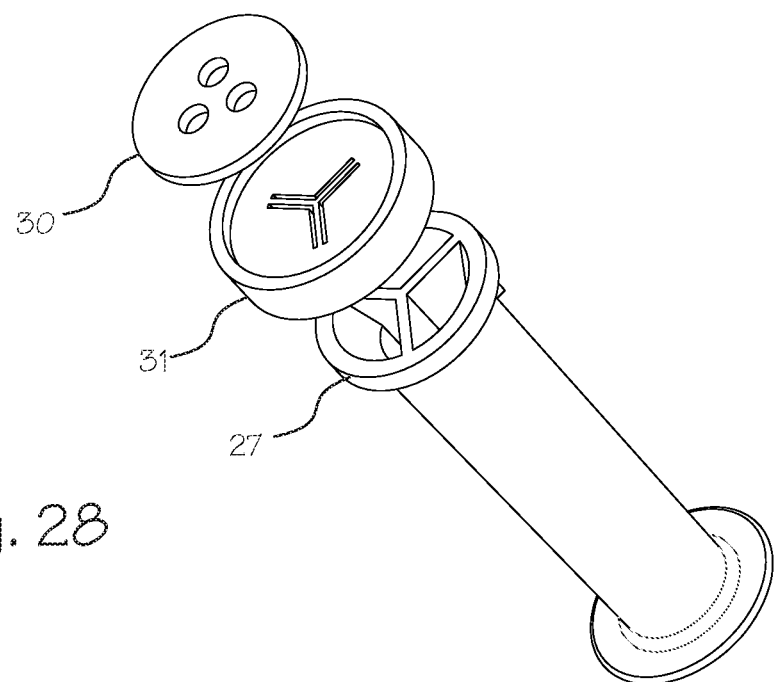
FIG. 28 illustrates an exploded view of a seal design for a multi-lumen cannula.
Figure 29:
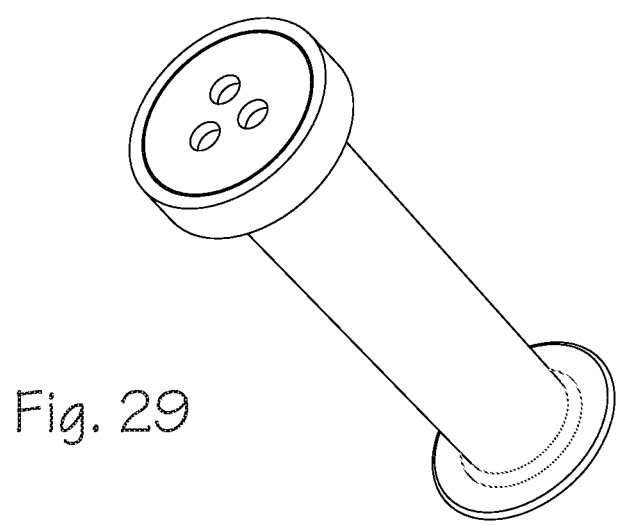
FIG. 29 illustrates a multi-lumen cannula.
Figure 30:
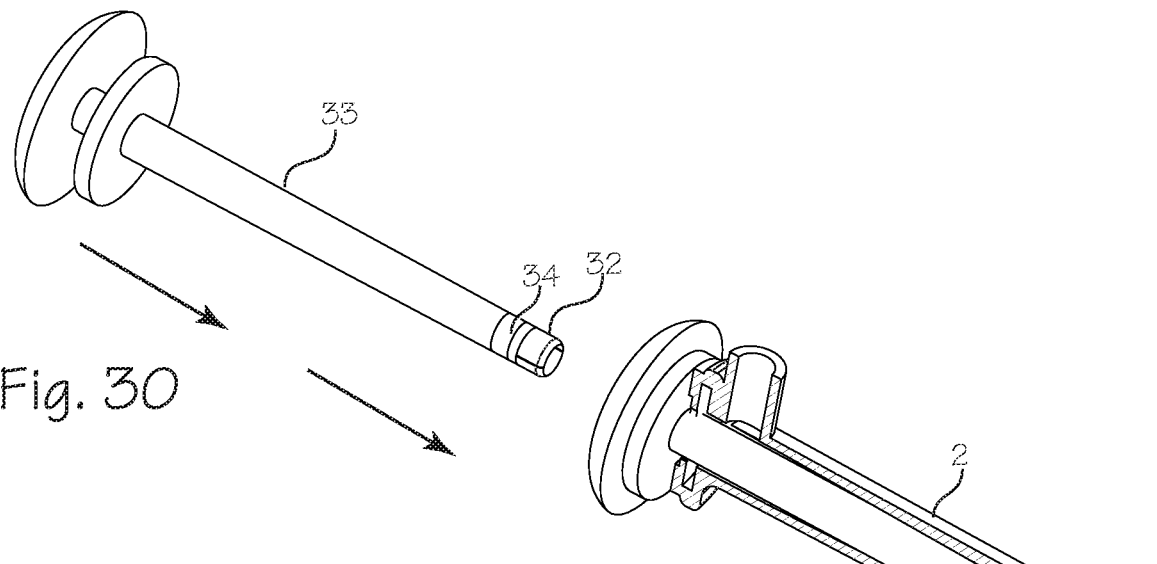
FIG. 30 illustrates a system using a spring-loaded driver.
Figure 31:
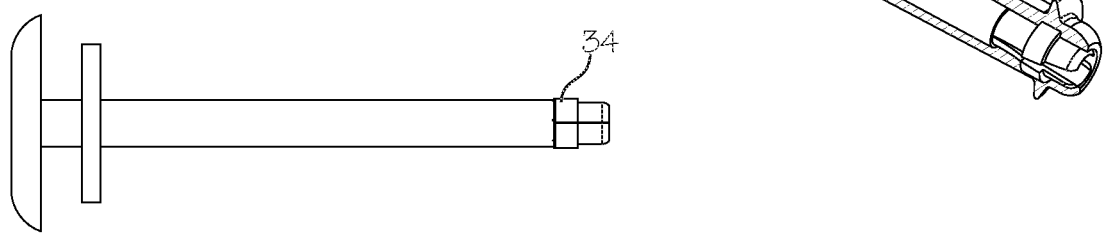
FIG. 31 illustrates a spring-loaded driver.
Figure 32:
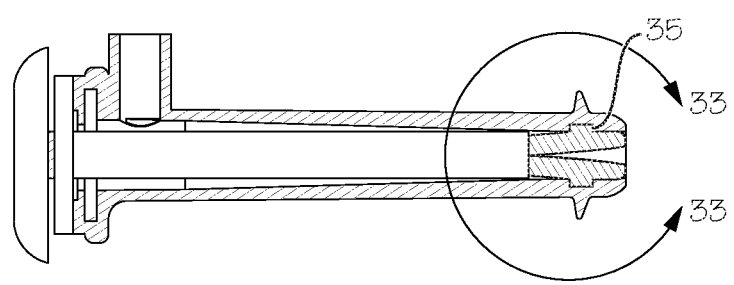
FIG. 32 illustrates a system using a spring-loaded driver.
Figure 33:
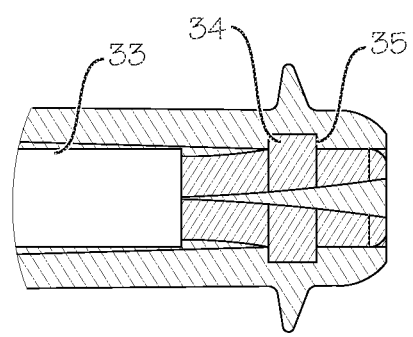
FIG. 33 is a detailed view of the mating engagement between the distal end of the spring-loaded driver and the cannula.

FIGS. 28 and 29 illustrates a seal design for use with a multiple lumen cannula for use with a single portal arthroscopy system. The round holes 30 act like traditional wiper seals found on standard cannulas, and the chevron shaped cuts 31 provide an additional seal behind the wiper seal that closes against the round hold with hydrostatic pressure. The design can also have a septum seal slit behind the wiper seal.

FIGS. 30 to 33 illustrates a driver with an expandable engagement mechanism. A spring steel inner driver 32 is disposed within a tube 33 wherein the spring steel inner driver expands when it is pushed out distally past the end of the tube. The expanding ring 34 disposed at the distal end of the driver engages an undercut feature 35 in the flexible cannula, allowing the flexible cannula to be pushed into a surgical portal. The driver collapses when released for easy removal. The driver may optionally be cannulated to accept a switching stick.

The cannulas described herein are a flexible portal made of an elastomer with a hardness range from Shore 10A to 40D. The material may be a moldable TPE (thermoplastic elastomer) or moldable silicone thermoset or thermoplastic elastomers (such as GLS Versaflex HC 2110-43N, PolyOne, Avon Lake Ohio) urethanes, Kraton, Santoprene, or liquid injection molded silicone, or compression molded silicone (such as Dow Corning C6-150 or C6-540). Because the portal is made of a flexible moldable material, the lumen can be molded to have a traditional circular cross section or a rectangular or square cross section to accommodate instruments with a rectangular or square cross section. For example, various devices for shoulder repair have square cross-sectional shafts rather than the traditional round shafts (example: the Tornier ArthroTunneler®). The square shafted instrument, in combination with a compatible cannula with a square cross section, results in a minimal cross-section when the instrument is placed therein.

Since the elastomer is tacky, the inner surface may be coated with a water-based biocompatible lubricant (available from AST Products (Billerica, Mass.) or Surmodics (Eden Prairie, Minn.)). The driver/obturator may be coated as well. In addition to the lubricious surface treatments, lubricious additives may be added to the cannula. These include any biocompatible additive to increase dry and wet lubricity of a molded low-durometer TPE, including barium and silicone oils. Other additives include PTFE powder and perfluoropolyether synthetic oil (available from Foster Corporation (Putnam, Conn.)).

Various seals can be used with the cannula, including a septum and wiper seal assembly 41, as shown in FIG. 18 and a triple flap seal 42 as shown in FIG. 25. The cannula may have a proximal fluid seal. The proximal seal may have a hemispherical shape to help the septum seal stay closed by hydrostatic pressure. The proximal fluid seal may be welded to the cannula with RF or ultrasonic welding if a TPE thermoplastic, or assembled by joining the silicone parts together before the thermoset is fully cured, and the parts weld together during the curing process. The seal and the cannula body may be molded of the same material, thus saving cost, and allowing thermoplastic TPE parts to be easily welded together.

Figure 34:
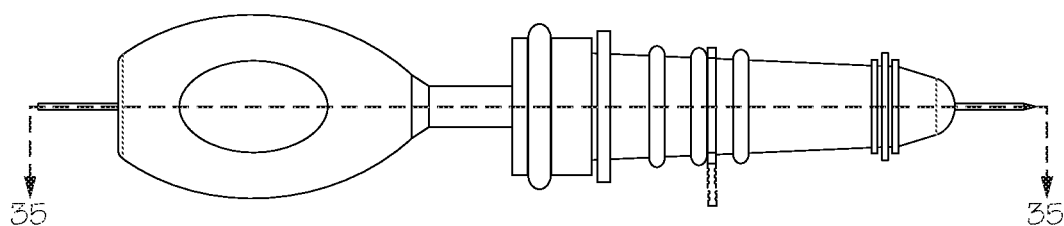
FIG. 34 illustrates a system using a removable O-ring and seal.
Figure 35:
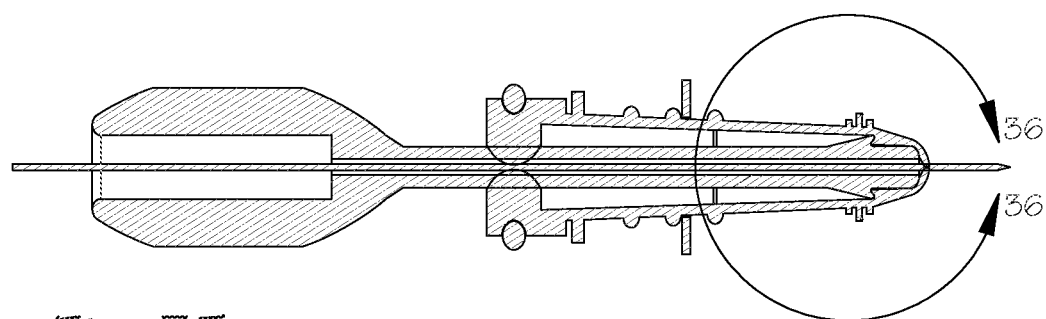
FIG. 35 illustrates a system using a removable O-ring and seal.
Figure 36:
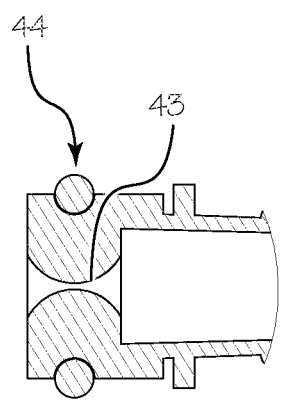
FIG. 36 illustrates a system using a removable O-ring and seal.
Figure 37:
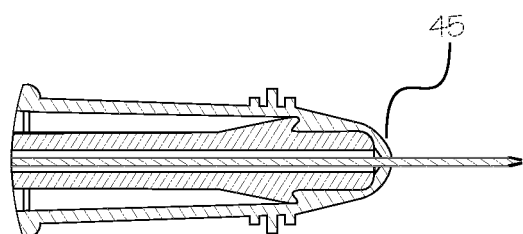
FIG. 37 illustrates a system utilizing a distal septum seal.

The cannula may have a sphincter-like seal 43 at the proximal end with a removable O-ring 44, as shown in FIGS. 34 to 36. When the O-ring is in place it makes a tight, reliable leak-resistant seal that is superior to a 3-layer septum seal. Also when the O-ring is removed, the seal will be easier to stretch open, allowing larger items to be passed through the seal such as biologic implants like sheet graft repairs constructs. It can also be held open with a tube or slotted cannula. FIG. 37 shows a distal septum seal 45.

Figure 38:
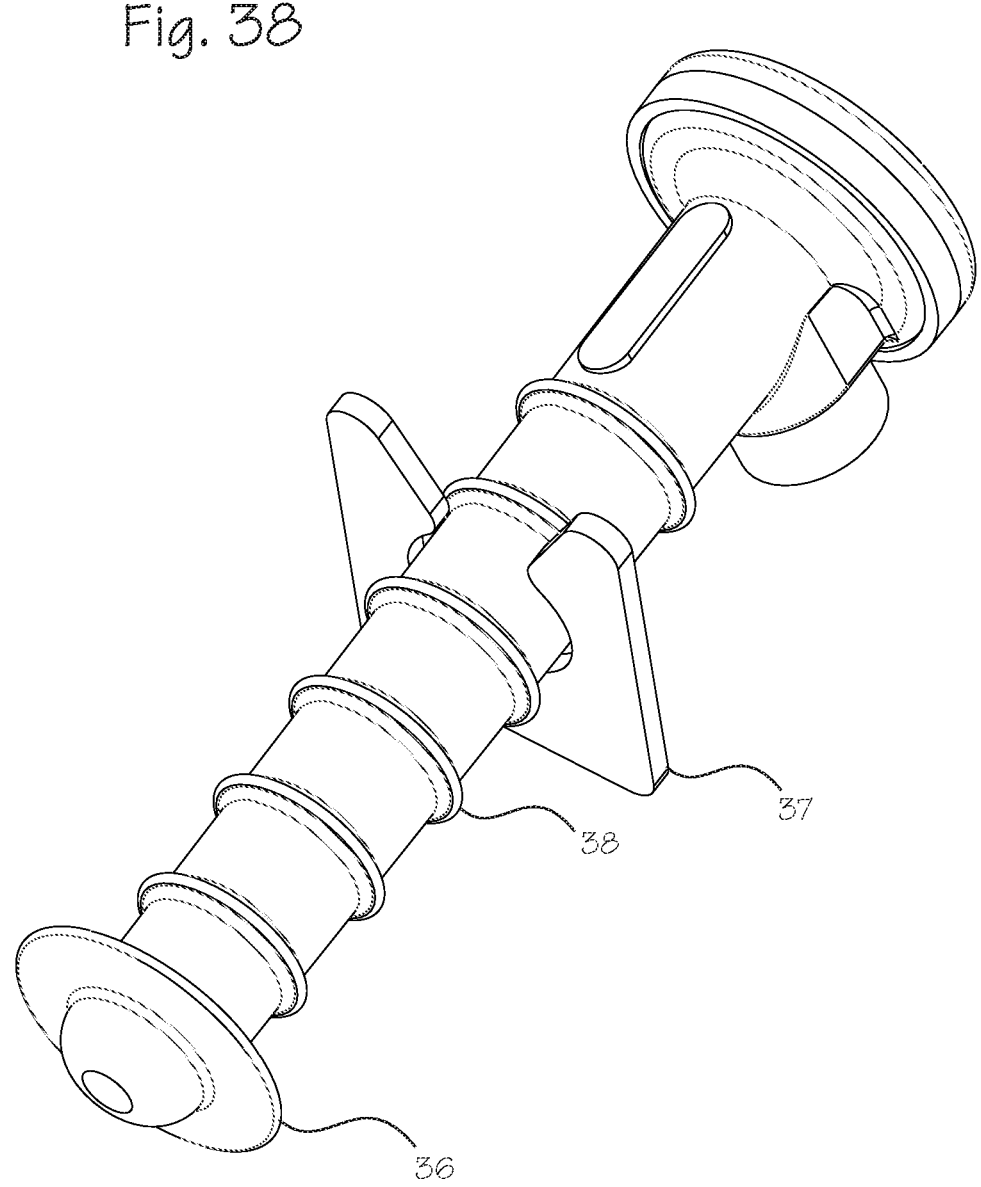
FIG. 38 illustrates a cannula with tissue compression and retraction.

FIG. 38 illustrates a cannula with a tissue compression and retraction feature. It is desirable to put traction on tissue inside the joint especially during labral (SLAP) repairs where tissue drops down and gets in the surgeons field of view. The elastomeric retention and retraction flange 36 folds back when the cannula is inserted. The distal flange 36 pulls this tissue back, and the side clip 37 keeps traction on the flange to keep the tissue retracted. Ridges 38 on the shaft of the cannula allow for incremental adjustment of compression and keep the clip from slipping. The clip can easily be slipped onto the cannula after insertion to the desired compression.

Generally, the cannula is a flexible portal cannula for use in conjunction with the cannula driver. The cannula driver comprises a shaft having a distal end and a proximal end and at least one distally extending projection extending from its distal end, or extending distally from the outer surface of the driver proximate its distal end. The flexible portal cannula comprises a flexible tube, characterized by a proximal end and a distal end and a lumen extending from the proximal end to the distal end of the flexible tube. The distal end of the flexible tube is adapted for insertion into a surgical site through a surgical portal. The flexible tube has a proximally facing groove disposed on an inner surface thereof, proximate its distal end, which is sized and dimensioned to receive a distally extending projection of the cannula driver. The proximally facing groove can be an annular groove entirely circumscribing the inner diameter of the portal cannula, or it may extend merely partially around the inner diameter. As illustrated, the groove is most conveniently formed by a ring extending proximally within the distal tip of the portal cannula. The ring can be suspended or fixed to an inwardly protruding flange which protrudes inwardly from the inner wall of the portal cannula, but can also be fixed directly to, or depend directly from, the inner wall of the portal cannula. The driver may be a solid shaft, but is preferably hollow, with a lumen suitable for passage of a switching stick. Also, the driver may be split longitudinally, into two or more elongate sections, to be used in conjunction with a portal cannula having two or more lumens separated by longitudinally extending webs, where the webs are sized to fit in the space separating the elongate sections, to provide a system for inserting multi-lumen portal cannulae.

While the preferred embodiments of the devices and methods have been described in reference to the environment in which they were developed, they are merely illustrative of the principles of the inventions. The elements of the various embodiments may be incorporated into each of the other species to obtain the benefits of those elements in combination with such other species, and the various beneficial features may be employed in embodiments alone or in combination with each other. Other embodiments and configurations may be devised without departing from the spirit of the inventions and the scope of the appended claims.

I claim:

1. A system for delivering a flexible cannula into the body for use in an arthroscopic procedure, said system comprising:
   a rigid driver, said rigid driver comprising a rigid tube with a lumen, a distal tip, and an outer surface, said rigid driver further comprising a distally extending protrusion disposed on the outer surface of the rigid tube just proximal to the rigid tube distal tip;
   a cannula, said cannula having a distal tip and a proximal end, said cannula further having a lumen, said distal tip having a proximally extending lip defining a groove sized and dimensioned to receive the distally extending protrusion of the rigid tube;
   said rigid tube distally extending protrusion engaging with the cannula proximally extending lip when the rigid driver is inserted through the proximal end of the cannula through the cannula lumen.

2. The system of claim 1 wherein the distally extending protrusion is parallel to the rigid tube outer surface.

3. The system of claim 1 wherein a distal most end of the distally extending protrusion is flared away from the rigid tube outer surface.

4. The system of claim 1 wherein said cannula further comprises a flexible flange positioned on the distal tip of the cannula, and wherein said cannula further comprises a retention system disposed about an outer surface of the cannula.

5. The system of claim 2 wherein said cannula further comprises a flexible flange positioned on the distal tip of the cannula, and wherein said cannula further comprises a retention system disposed about an outer surface of the cannula.

6. The system of claim 3 wherein said cannula further comprises a flexible flange positioned on the distal tip of the cannula, and wherein said cannula further comprises a retention system disposed about an outer surface of the cannula.

7. The system of claim 4 wherein said retention system comprises a plurality of retention features consisting of a series of ridges circumferentially disposed around the outer surface of the cannula.

8. The system of claim 5 wherein said retention system comprises a plurality of retention features consisting of a series of ridges circumferentially disposed around the outer surface of the cannula.

9. The system of claim 6 wherein said retention system comprises a plurality of retention features consisting of a series of ridges circumferentially disposed around the outer surface of the cannula.

10. A method of delivering a flexible cannula into the body for use in an arthroscopic procedure, said method comprising:
    providing a rigid driver, said rigid driver comprising a rigid tube with a lumen, a distal tip, and an outer surface, said rigid driver further comprising a distally extending protrusion disposed on the outer surface of the rigid tube just proximal to the rigid tube distal tip;
    providing a cannula, said cannula having a distal tip and a proximal end, said cannula further having a lumen, said distal tip having a proximally extending lip defining a groove sized and dimensioned to receive the distally extending protrusion of the rigid tube;
    providing a switching stick;
    inserting the rigid driver through the lumen of the cannula, wherein said distally extending protrusion engages with the cannula proximally extending lip, and wherein the rigid driver distal tip extends beyond the cannula distal tip;
    inserting the switching stick through the lumen of the rigid driver;
    inserting the switching stick into a surgical portal until the cannula is in a desirable position;
    withdrawing the switching stick; and
    withdrawing the rigid driver.

11. The method of claim 10 wherein the distally extending protrusion is parallel to the rigid tube outer surface.

12. The method of claim 10 wherein a distal most end of the distally extending protrusion is flared away from the rigid tube outer surface.

13. The method of claim 10 wherein said cannula further comprises a flexible flange positioned on the distal tip of the cannula, and wherein said cannula further comprises a retention system disposed about an outer surface of the cannula.

14. The method of claim 11 wherein said cannula further comprises a flexible flange positioned on the distal tip of the cannula, and wherein said cannula further comprises a retention system disposed about an outer surface of the cannula.

15. The method of claim 12 wherein said cannula further comprises a flexible flange positioned on the distal tip of the cannula, and wherein said cannula further comprises a retention system disposed about an outer surface of the cannula.

16. The method of claim 13 wherein said retention system comprises a plurality of retention features consisting of a series of ridges circumferentially disposed around the outer surface of the cannula.

17. The method of claim 14 wherein said retention system comprises a plurality of retention features consisting of a series of ridges circumferentially disposed around the outer surface of the cannula.

18. The method of claim 15 wherein said retention system comprises a plurality of retention features consisting of a series of ridges circumferentially disposed around the outer surface of the cannula.

19. The method of claim 16 wherein said method further comprises providing a clip, said clip slipped onto the outer surface of the cannula after insertion of the cannula to the desired position.

20. The method of claim 17 wherein said method further comprises providing a clip, said clip slipped onto the outer surface of the cannula after insertion of the cannula to the desired position.

21. The method of claim 18 wherein said method further comprises providing a clip, said clip slipped onto the outer surface of the cannula after insertion of the cannula to the desired position.

* * * * *